United States Patent [19]

Oneda et al.

[11] Patent Number: 4,979,498

[45] Date of Patent: Dec. 25, 1990

[54] VIDEO CERVICOSCOPE SYSTEM

[75] Inventors: Katsumi Oneda, Alpine; Isao Fujimoto, Cresskill, both of N.J.

[73] Assignee: Machida Incorporated, Orangeburg, N.Y.

[21] Appl. No.: 429,091

[22] Filed: Oct. 30, 1989

[51] Int. Cl.[5] .............................................. A61B 1/06
[52] U.S. Cl. ........................................... 128/6; 128/7; 128/23
[58] Field of Search .............................. 128/4, 6, 7, 23

[56] References Cited

U.S. PATENT DOCUMENTS

| | | | |
|---|---|---|---|
| 4,646,722 | 3/1987 | Silverstein et al. | 128/4 |
| 4,651,202 | 3/1987 | Arakawa | 128/6 X |
| 4,790,295 | 12/1988 | Tashiro | 128/6 |
| 4,819,620 | 4/1989 | Okutsu | 128/6 X |
| 4,878,485 | 11/1989 | Adair | 128/6 |

Primary Examiner—William H. Grieb
Attorney, Agent, or Firm—Kane, Dalsimer, Sullivan, Kurucz, Levy, Eisele and Richard

[57] ABSTRACT

This invention is directed to a video cervicoscope system. More particularly, this invention is directed to a video cervicoscope system for the examination of the cervix comprising:
  a rigid, elongated tubular member having a light guide;
  imaging means at the distal end of said tubular member,
  a disposable, light-transmitting, sleeve diposed about the distal end of said tubular member; and
  transmitting means to transmit an image viewed by said imaging means proximally to a control box wherein said image is received and stored.

13 Claims, 3 Drawing Sheets

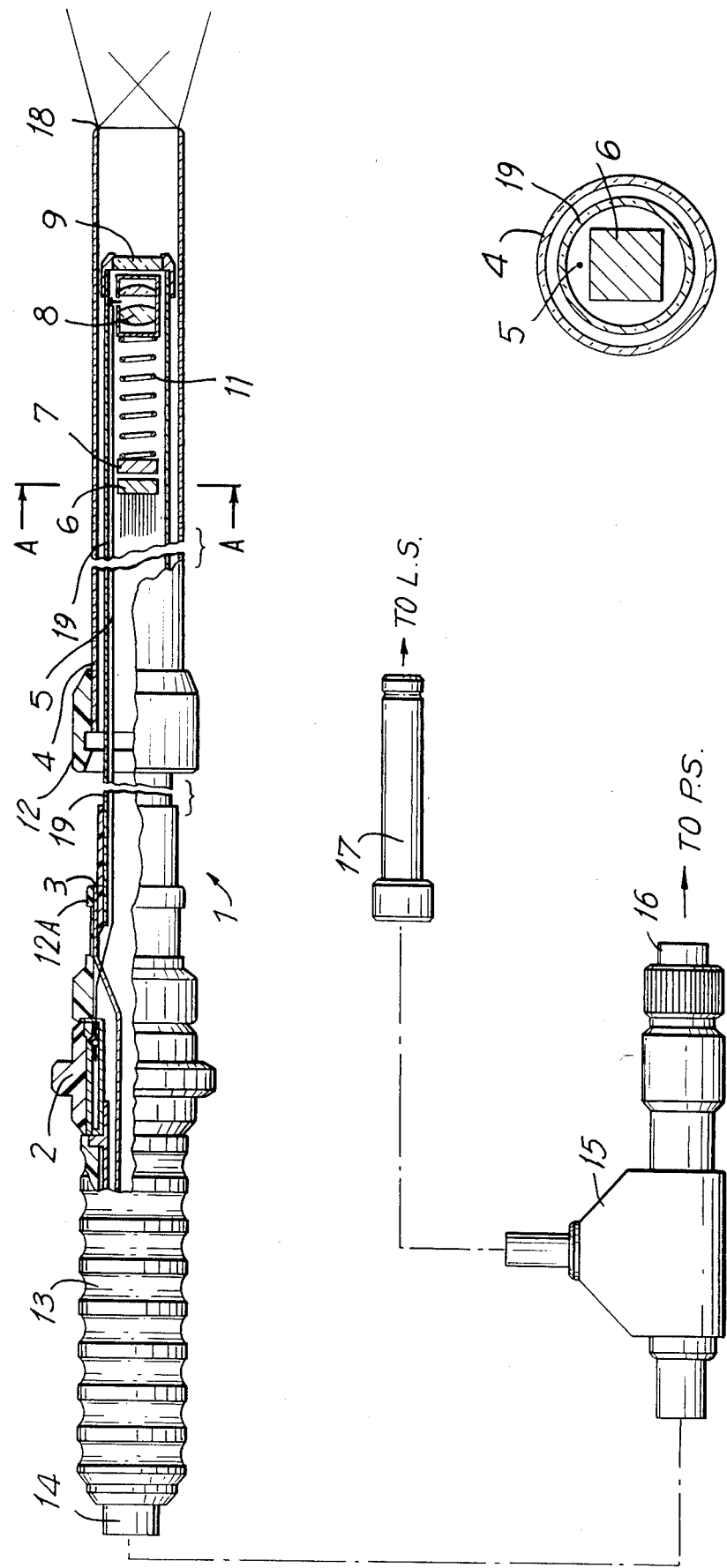

VIDEO CERVICOSCOPE SYSTEM

FIELD OF THE INVENTION

This invention is directed to a video cervicoscope system. More particularly, this invention is directed to a video cervicoscope system comprising a rigid video cervicoscope, a light transmitting disposable sleeve, and means for receiving and storing images.

BACKGROUND OF THE INVENTION

Cervical exams are performed in adult women to detect problems, such as cancer, before any symptoms are evident. Such exams are performed by a doctor, with a nurse in attendance. The patient's legs are spread and elevated on stirrups, and internal inspection requires a light source and a metal or plastic speculum. The speculum spreads the walls of the vagina so that the inside may be observed. A Pap smear is also performed through the speculum, with a stick similar to a tongue depressor, and sometimes a culture is taken with a cotton swab. Should any abnormalities be detected, such as chronic cervicitis or cervical polyps, a colposcope or colpumiroscope is used to do a more thorough examination.

The physical position that the patient must assume can be uncomfortable and somewhat embarrassing. This may cause tension at a time when it is necessary for the patient to relax her vaginal muscles. Also, the doctor must put his or her face close to the vagina to view through the speculum. One must question the effectiveness of such an exam since its comparable to looking into a tunnel with a flashlight.

A more detailed exam can be done with a colposcope, which is similar to a small microscope with a swing arm. The scope section is inserted into the vagina for a detailed look. This procedure, colposcopy, is only a live view, without any effective method of documenting or reviewing what has been observed.

OBJECTS OF THE INVENTION

It is an object of this invention to provide an improved procedure whereby the patient is in a less awkward position.

It is also an object of this invention to provide a procedure whereby improved viewing of the cervix can be provided on a monitor for physicians as well as patients.

It is a yet further object of this invention to provide documentation of a cervical examination by storing images on a floppy disc or VCR tape.

It is additionally an object of the invention to provide a rigid video cervicoscope system for the observing the cervix comprising:
- a rigid, elongated tubular member having an imaging means at its distal end;
- a disposable light transmitting sleeve disposed over the distal end of the tubular member; and
- means for receiving and storing images.

These and other objects of the invention will become more apparent from the discussion below.

BRIEF DESCRIPTION OF THE DRAWINGS

FIG. 1 is an exploded, partial, longitudinal cross-sectional view of a video cervicoscope according to the invention;

FIG. 2 is a cross-sectional view along line A—A in FIG. 1;

DETAILED DESCRIPTION OF THE INVENTION

Figure 3:
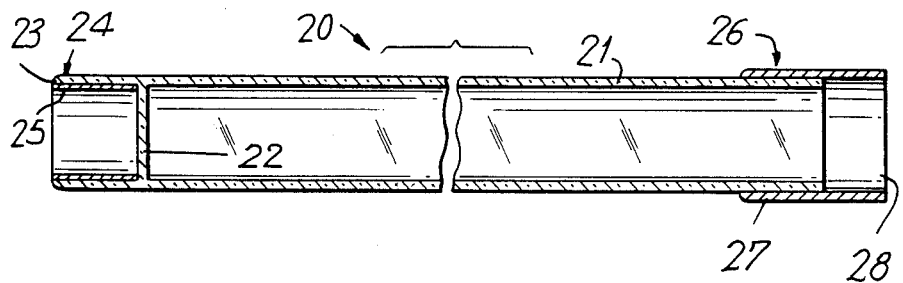
FIGS. 3, 4, and 5 are each a longitudinal cross-sectional view of a disposable sleeve useful according to the invention.

The invention herein is directed to a video cervicoscope system comprising a video cervicoscope, disposable, light-transmitting sleeve, and associated equipment for receiving, storing, and printing images generated. The invention is unique in that it allows the physician to position himself or herself next to the patient during a cervical examination rather than between the patient's legs. Viewing takes place through the use of a color CCD (charge coupled device) chip endoscope, which allows the physician to view the cervix on a high resolution monitor and then capture and store data as desired. Pictures can be printed immediately for the physician's or patient's use. Also, the invention herein is particularly adapted for measurement of cervical dilation, as prior to delivery of a baby.

By use of sterile disposable sleeves over the insertion tube of the video cervicoscope, cleaning time is either reduced significantly or eliminated altogether and the possibility of cross-contamination is eliminated. Also, the distal tip of the sleeve can be configured to provide the physician with the capability of taking a tissue sample at any time during the procedure.

The video cervicoscope useful according to the invention comprises a rigid elongated tubular member having a light transmitting sleeve disposed thereon and an annular light guide engaging the proximal end of the sleeve. In the distal end of the tubular member is imaging means such as a CCD chip, which imaging means communicates with transmission means which transmits images in the proximal direction to a control box for receiving and storing images. Said transmission means also communicates with a light source to illuminate the annular light guide. The control box may comprise a computer to receive, store, and/or retrieve images, text, voice commentary, and other important data, as well as a high resolution RGB monitor for viewing. It should be noted that the video cervicoscope itself has sufficient internal integrity to be soakable for any necessary cleaning.

It is envisioned that at least three variations of the disposable sleeve can be useful according to the invention. In one embodiment a disposable sleeve would comprise a hollow tube open at each of its proximal and distal ends. The proximal end would be configured so that when the sleeve is slid over the distal end of the video cervicoscope, the proximal end of the sleeve is releasably secured to the video cervicoscope. For example, the distal end of the sleeve and the video cervicoscope could merely form a snug, friction fit. In a variation of the aforementioned embodiment, there would be a substantially flat, clear surface perpendicular to the longitudinal axis of the sleeve and capable of image transmission without substantial distortion.

The flat, clear surface can be a separate rigid piece glued or affixed to the sleeve. In the alternative, the flat, clear surface could possibly be formed in the sleeve during manufacture.

In a third embodiment of the sleeve, the sleeve has a second, working channel extending substantially the length of the sleeve. This working channel, suitable for introduction of a forceps or other instrument for obtaining tissue samples or for another scope, such as a microcoloposcope, preferably is tapered so that the cross-section of the proximal end of the working channel is greater than that of the distal end.

The sleeve is made from light transmitting polymeric material suitable for transmitting light from an annular light means located on the video cervicoscope to the area to be examined, i.e., the cervix. Many polymers and copolymers would be suitable for this purpose. Examples of such suitable materials include polyacrylates, polycarbonates, and copolymers thereof.

The sleeve itself will be transparent or translucent. In a preferred embodiment of the invention, the inner surface of the distal end of the sleeve is opaque. This can be achieved by either coating this interior surface with a suitable material, such as black paint, or by inserting a separate, opaque tubular member, which would fit snugly within the distal portion of the sleeve. In one variation of the invention, such an opaque member may have a flat, clear surface sealingly affixed to its proximal end.

Use of a sleeve as described above on a video cervicoscope would assure the physician and the patient that cross-contamination, and thus the spread of AIDS or another communicable disease, does not occur. Since a soiled sleeve can be removed after use and then readily replaced by a sterile one for new use, the use of such disposable sleeves would eliminate, if not drastically reduce, the time and expense incurred in cleaning and disinfecting such scopes.

The transmission means, that is, the "umbilical cord" from the video cervicoscope, would communicate with a control box and an incoherent light source. The control box would consist of a video processor, video floppy or VCR, and monitor and has an interface for a computer image management system ("IMS"), video-frame printer, and keyboard for patient information. The control box may optionally have a device to produce hard copy prints. An example of such a device is Sony Mavigraph, which can generate prints in 60 seconds.

The hard copy prints can be made to show the patient any pathology found. Also, the patient could use these prints to discuss the pathology with family members. The physician may use this documentation for consultation with other physicians or surgeons. Furthermore, this system allows for permanent storage on floppy discs in the event of any medical/legal situation which may arise.

The above system would be particularly effective in following up on post-cancer patients or DES patients, who have a very high risk of developing cervical cancer. Such a system would facilitate follow-up and documentation of tissue changes in such patents.

The invention can perhaps be understood by making reference to the drawings. In FIG. 1, a video cervicoscope 1 comprises a rigid tubular member 19 extending substantially the length of cervicoscope 1 and terminating distally in cover glass 9. Proximal of the cover glass 9 are one or more lens 8. Lens 8 cooperate with CCD chip 6, and CCD chip 6 and lens 8 are movingly separated by spring means 11. Spring means 11 can be adjusted by ring focus adjustment 2, which is connected to spring means 11 by focus adjustment wire 5. Optionally a filter such as blue filter 7 may be present distal of CCD chip 6.

Disposable sleeve 4 slides proximally so that the proximal end of sleeve 4 engages or communicates with light guide 3. Here, the proximal end of sleeve 4 has a fitting 12 which engages a reciprocal fitting 12A.

Images seen by CCD chip 6 are transmitted through cable 14 proximally from cervicoscope 1 to connector 15 and through wire 16 to a control box. Light from a light source is transmitted distally through optic fiber 17 to connector 15 and through cable 14 to the annular light guide 3 on cervicoscope 1.

In a preferred embodiment of the invention shown, the proximal portion of cervicoscope 1 comprises a gripping means 13 having ribbed or otherwise textured surface. Also, the distal end of sleeve 4 has a sharp interior edge 18 useful for scraping tissue samples.

FIG. 2 represents a longitudinal cross-section of a portion of the cervicoscope 1 shown in FIG. 1. It can be seen in said cross-section that CCD chip 6 is approximately square in shape and is surrounded by light transmitting sleeve 4.

Figure 4:
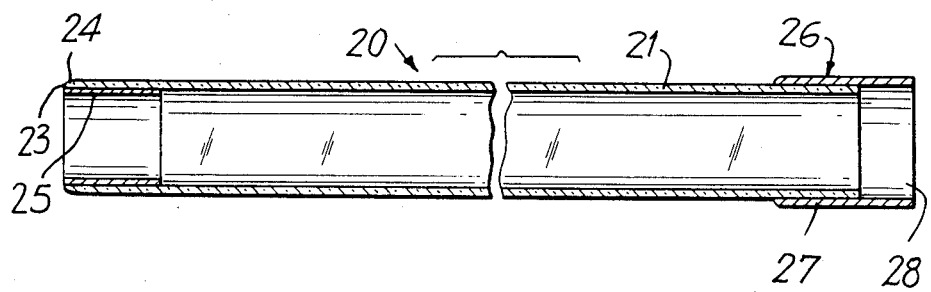
Figure 5:
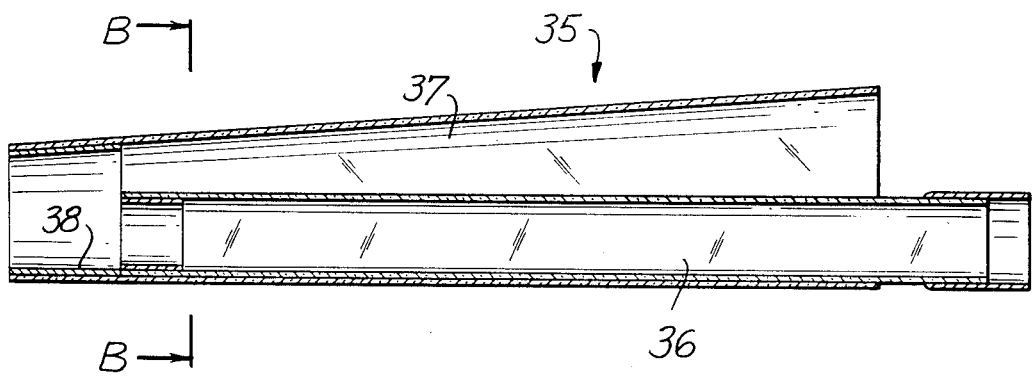

FIGS. 3, 4, and 5 represent sleeves useful according to the invention. In FIG. 3 the disposable sleeve 20 comprises a tubular member 21 having a rigid clear cover glass member 22. The inner surface 23 of the distal end 24 of tubular member 21 has an opaque, preferably black, coating 25 to provide better image definition. Optionally, instead of an opaque coating there may be a short tubular member of opaque, preferably black, material inserted into the distal end 24. At the proximal end 26 of tubular member 21 there may optionally be present fitting means 27 for securing sleeve 20 to the exterior of a video cervicoscope. Fitting means 27 may comprise an opaque sleeve 28.

FIG. 4 represents a variation of the sleeve shown in FIG. 3 where cover glass member 22 is not present.

In FIG. 5, the disposable sleeve 35 has channel 36 for a video cervicoscope and working channel 37. This working channel 37 is open the length of sleeve 35 to permit introduction of biopsy forceps or other instrumentation, such as a microcoloposcope (not shown). Channel 36 would substantially conform to sleeves 20 described above in FIGS. 3 and 4. Working channel 37 would be tapered outwardly in the proximal direction. Also, working channel 37 may have an opaque coating or inner tubular member 38.

Figure 6:
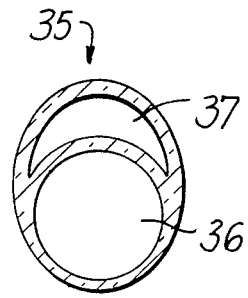
FIG. 6 is a cross-sectional view of the sheath shown in FIG. 5.

FIG. 6 represents a cross-sectional view of sleeve 35 across line A—A of FIG. 1.

Figure 7:
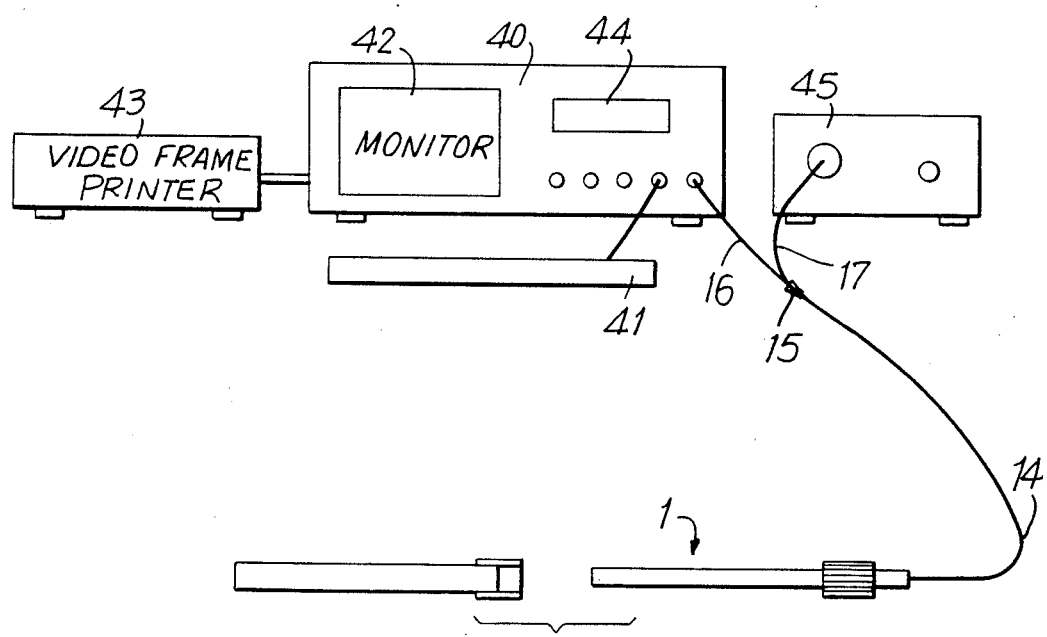
FIG. 7 is a schematic representation of the video cervicoscope system of the invention.

FIG. 7 is a rough schematic diagram showing the manner in which the video signal from cervicoscope 1 can be processed. For example, the video image from cervicoscope 1 can be transmitted via wire in cable 14 to connector 15 through wire 16 to control box 40. Control box 40 is connected to keyboard 41 as well as to monitor 42. Control box 40 can optionally be connected to printer 43 for making hard copies. Also, control box has a floppy disc or VCR 44.

Light source 45 provides incoherent light that is transmitted through optic fiber 17 to connector 15 and then through optic fiber in cable 14 to annular light ring 3.

A cervicoscope useful according to the invention can be from about 20 to 60 cm in length, preferably from about 25 to 45 cm in length. The cervicoscope will be substantially cylindrical, having a diameter of from about 2 to 6 cm, preferably from 2.5 to about 5 cm. The disposable sleeve would extend from the distal end of the cervicoscope approximately ⅛ to ¾ of the length of the cervicoscope. The disposable sleeve would have a thickness suitable to prevent breaking, preferably from about 0.5 to 3.0 mm, more preferably from about 1.0 to 2.0 mm.

The preceding specific embodiments are illustrative of the practice of the invention. It is to be understood, however, that other expedients known to those skilled in the art or disclosed herein, may be employed without departing from the sprint of the invention or the scope of the appended claims.

I claim:

1. A rigid video cervicoscope system for the examination of the cervix, comprising:
    a rigid elongated tubular member having proximal and distal ends and having a light guide disposed toward said proximal end;
    imaging means at the distal end of said tubular member;
    a disposable sleeve having proximal and distal ends disposed about at least the distal end of said tubular member, the proximal end of said sleeve being adapted to be positioned adjacent to the light guide so that light is transmitted distally substantially through the wall of the sleeve to illuminate a viewing area; and
    transmitting means to transmit an image viewed by said imaging means proximally to a control box wherein said image is received and stored.

2. The system of claim 1, wherein the distal end of the disposal sleeve comprises a cover glass.

3. The system of claim 1, wherein the light guide is an annular light ring.

4. The system of claim 1, wherein the proximal end of the sleeve is adapted to be releasably fitted to the cervicoscope.

5. The system of claim 4, wherein the proximal end of the sleeve and the cervicoscope have reciprocally engaging fittings.

6. The system of claim 1, wherein the sleeve also comprises a working channel extending at least the length of the sleeve.

7. The system of claim 1, wherein the imaging means comprises a lens at the distal end of the cervicoscope and a color CCD chip positioned proximal to the lens.

8. The system of claim 7 which comprises adjusting means for adjusting the relative distance between the lens and the CCD chip.

9. The system of claim 7, wherein a light filter is positioned proximal to the CCD chip.

10. The system of claim 1, wherein the light guide is connected to a light source.

11. The system of claim 1, wherein the control box comprises a processor, a monitor, and a video floppy disc and/or VCR.

12. The system of claim 11, wherein the monitor is an RGB monitor.

13. The system of claim 1, wherein the control box is connected to a hard copy printer.

* * * * *